United States Patent [19]
Suzuki et al.

[11] Patent Number: 5,902,284
[45] Date of Patent: May 11, 1999

[54] MEDICAL INDWELLING TUBE

[75] Inventors: Yasuyuki Suzuki; Yasuo Miyano, both of Hachioji; Yoshio Onuki, Tokyo, all of Japan

[73] Assignee: Olympus Optical Co., Ltd., Tokyo, Japan

[21] Appl. No.: 08/867,896

[22] Filed: Jun. 3, 1997

[30]    Foreign Application Priority Data

Jun. 14, 1996  [JP]  Japan .................................. 8-153857
May 28, 1997  [JP]  Japan .................................. 9-153062

[51] Int. Cl.⁶ .................................................... A61M 5/35
[52] U.S. Cl. ............................................................ 604/265
[58] Field of Search .................................. 604/265, 264, 604/266; 623/1

[56]           References Cited

U.S. PATENT DOCUMENTS

| 3,965,909 | 6/1976 | Waddell et al. . | |
| 4,592,341 | 6/1986 | Omagari et al. . | |
| 5,176,626 | 1/1993 | Soehendra . | |
| 5,752,941 | 5/1998 | Romano et al. ........................ | 604/265 |
| 5,772,640 | 6/1998 | Modak et al. ........................... | 604/265 |

FOREIGN PATENT DOCUMENTS

| 21 56 994 | 5/1973 | Germany . |
| 28 11 591 C2 | 9/1979 | Germany . |
| 38 30 359 A1 | 12/1989 | Germany . |
| 44 29 380 C1 | 4/1996 | Germany . |
| 60-180442 | 11/1985 | Japan . |
| 62-26787 | 6/1987 | Japan . |
| 5-192389 | 8/1993 | Japan . |
| 6-1706 | 1/1994 | Japan . |

OTHER PUBLICATIONS

D. Ushiba, Saikingaku Nyumon (Introduction to Medical Bacteriology), published by Nanzando Co., Ltd., Tokyo, Japanese Title Pg., English–language Title Pg., Copyright Notice Page, 1st pg. Chapter 13, Chapter 18, pp. 158–159, and Index p. 384.

*Primary Examiner*—John D. Yasko
*Attorney, Agent, or Firm*—Frishauf, Holtz, Goodman, Langer & Chick, P.C.

[57]           ABSTRACT

A medical indwelling tube for forming a passage at a predetermined portion where the tube is placed comprising a tube member having at least an inner surface portion of an inner cavity formed of thermal plastic resin, and means for setting surface roughness of the inner surface of the tube member to 0.5 $\mu$m or less by an expression of maximum height Ry, thereby preventing deposition of bacteria and matters in body fluids on the inner surface of the tube caused by a bacteria adhering phenomenon.

7 Claims, 14 Drawing Sheets

200 MAGNIFICATION OF SURFACE OF
SAMPLE A BEFORE EXPERIMENT

5000 MAGNIFICATION OF SURFACE OF
SAMPLE A AFTER EXPERIMENT

30000 MAGNIFICATION OF SURFACE OF
SAMPLE A AFTER EXPERIMENT
F I G. 11
200 MAGNIFICATION OF SURFACE OF
SAMPLE B BEFORE EXPERIMENT
F I G. 12

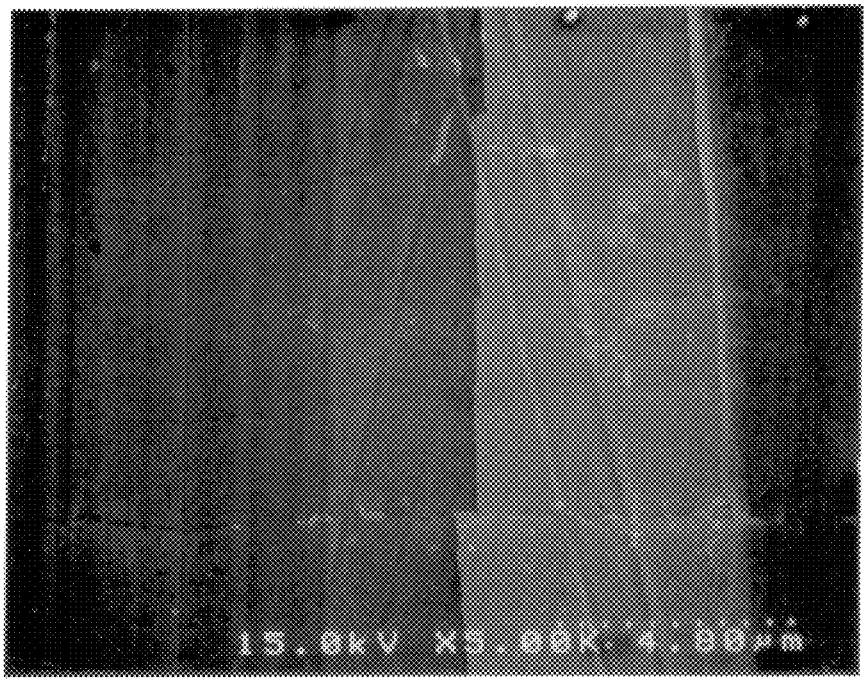
5000 MAGNIFICATION OF SURFACE OF
SAMPLE B AFTER EXPERIMENT
F I G. 13
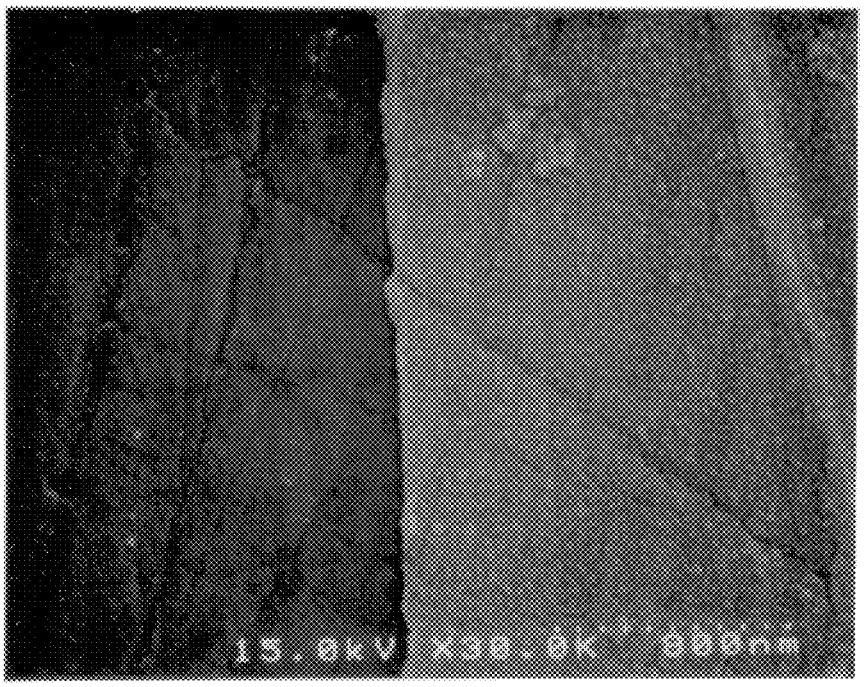
30000 MAGNIFICATION OF SURFACE OF
SAMPLE B AFTER EXPERIMENT
F I G. 14

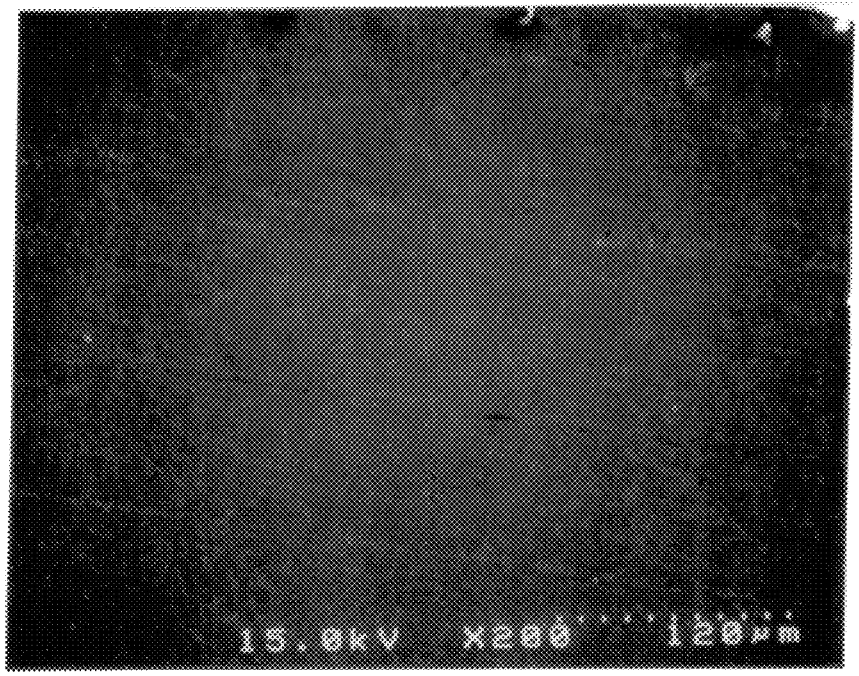
200 MAGNIFICATION OF SURFACE OF
SAMPLE C BEFORE EXPERIMENT
F I G. 15
5000 MAGNIFICATION OF SURFACE OF
SAMPLE C AFTER EXPERIMENT
F I G. 16

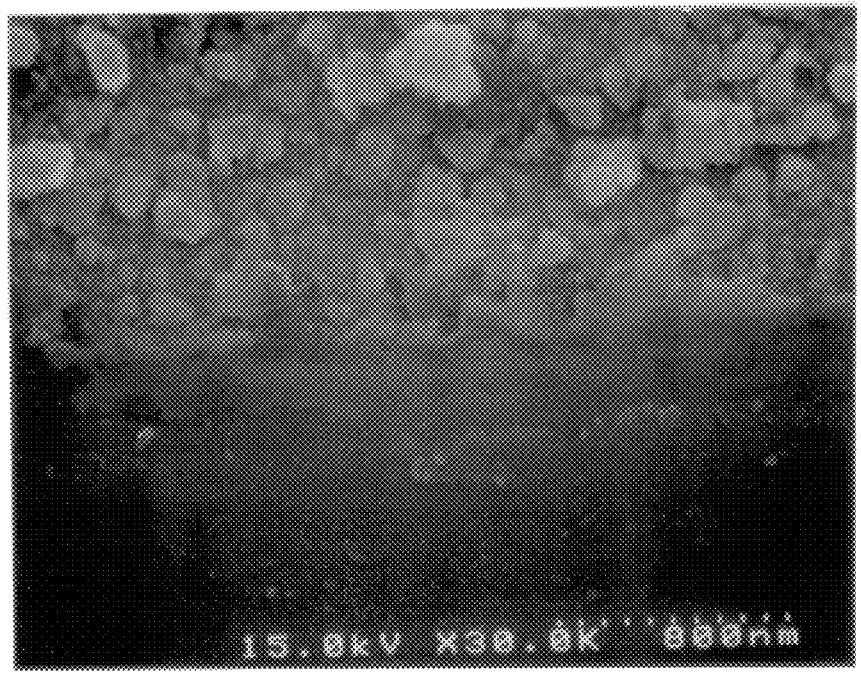
3000 MAGNIFICATION OF SURFACE OF
SAMPLE C AFTER EXPERIMENT
F I G. 17
200 MAGNIFICATION OF SURFACE OF
SAMPLE D BEFORE EXPERIMENT
F I G. 18

5000 MAGNIFICATION OF SURFACE OF
SAMPLE D AFTER EXPERIMENT

30000 MAGNIFICATION OF SURFACE OF
SAMPLE D AFTER EXPERIMENT

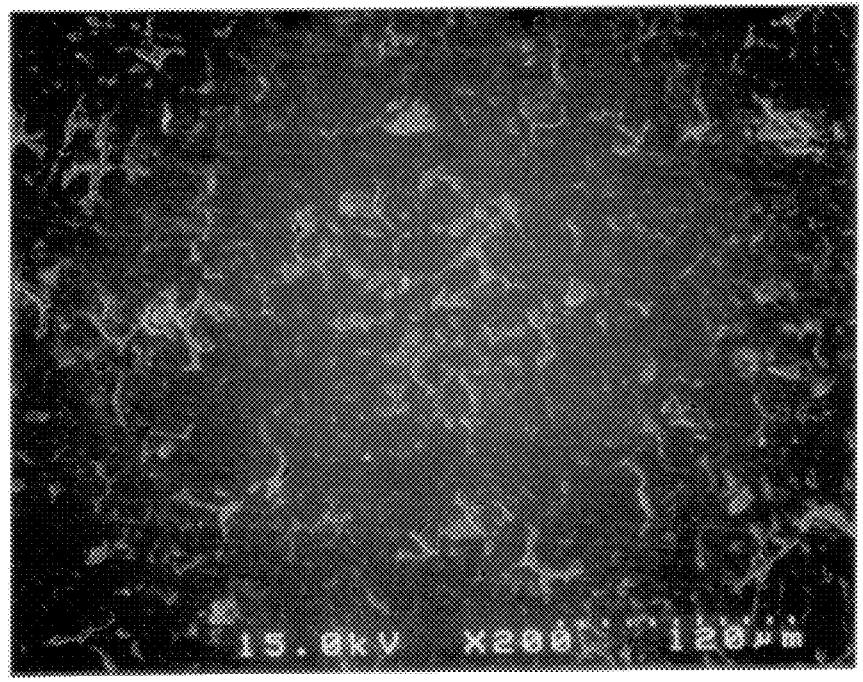
200 MAGNIFICATION OF SURFACE OF
SAMPLE E BEFORE EXPERIMENT
F I G. 21
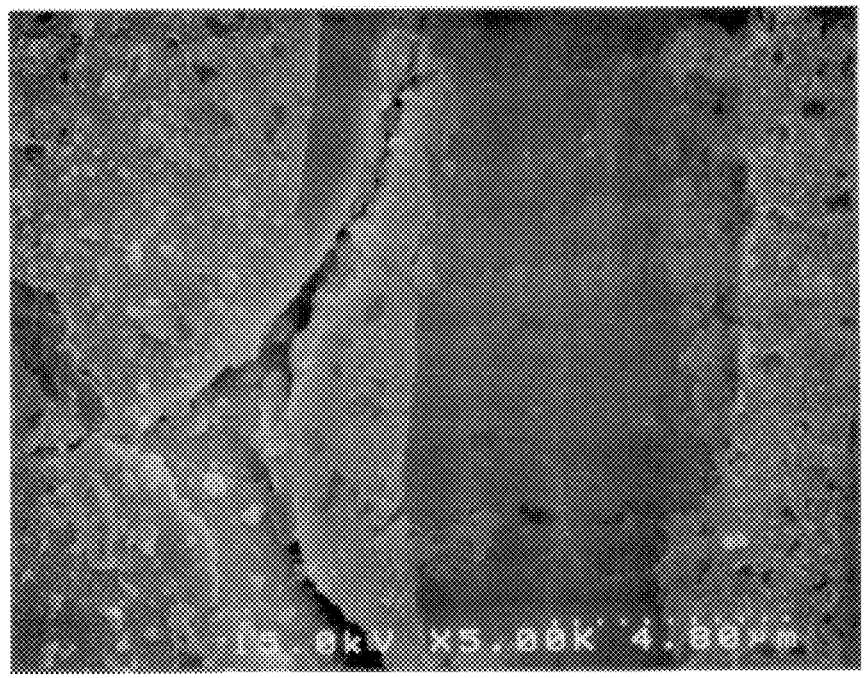
5000 MAGNIFICATION OF SURFACE OF
SAMPLE E AFTER EXPERIMENT
F I G. 22

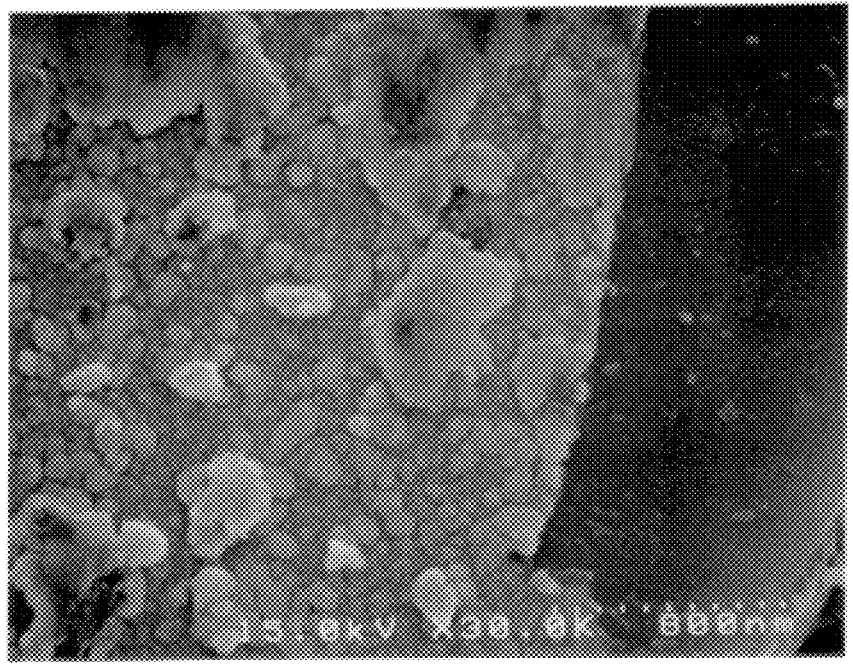
30000 MAGNIFICATION OF SURFACE OF
SAMPLE E AFTER EXPERIMENT
F I G. 23
200 MAGNIFICATION OF SURFACE OF
SAMPLE F BEFORE EXPERIMENT
F I G. 24

5000 MAGNIFICATION OF SURFACE OF SAMPLE F AFTER EXPERIMENT

30000 MAGNIFICATION OF SURFACE OF SAMPLE F AFTER EXPERIMENT

200 MAGNIFICATION OF SURFACE OF
SAMPLE G BEFORE EXPERIMENT
F I G. 27
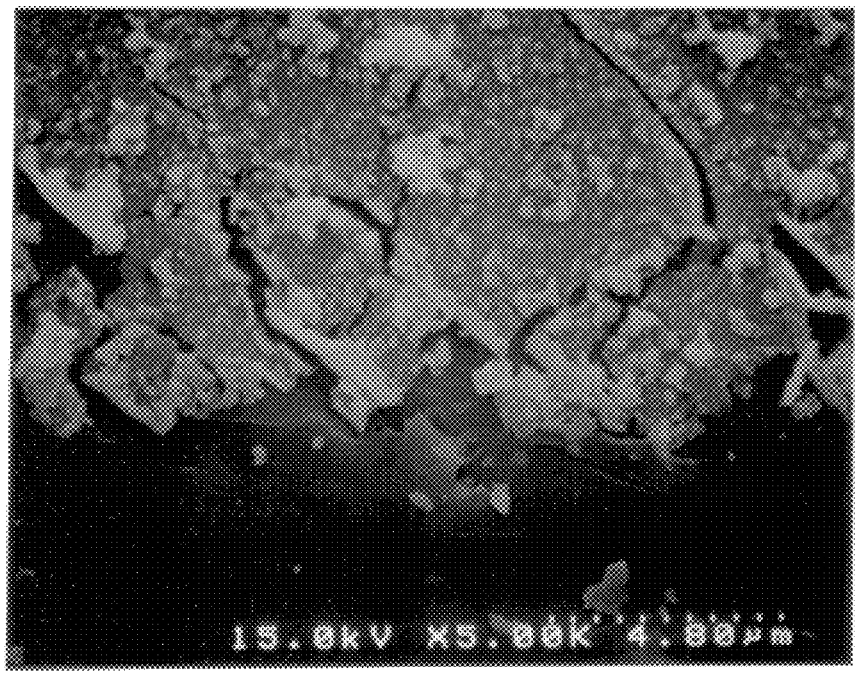
5000 MAGNIFICATION OF SURFACE OF
SAMPLE G AFTER EXPERIMENT
F I G. 28

30000 MAGNIFICATION OF SURFACE OF SAMPLE G AFTER EXPERIMENT

MEDICAL INDWELLING TUBE

BACKGROUND OF THE INVENTION

The present invention relates to a medical indwelling tube, which is inserted to a human body to be positioned at a predetermined position such as a biliary duct and a pancreatic duct, for forming a passage for passing body fluid such as bile and pancreatic juice.

Coventry, a drainage tube for a biliary duct, catheter are known as a medical indwelling tube.

The drainage tube for a biliary duct is positioned at a strangulated biliary duct to discharge bile. For example, in Japanese Utility Model KOKAI Publication No. 60-180442, there is proposed a drainage tube for a bile, which is formed of polyethylene.

Also, as the drainage tube for a biliary duct, there is proposed a double tube structure having an outer tube forming an engaging flap and an inner tube formed of fluorine resin in Japanese Utility Model KOKOKU Publication No. 6-1706 and Japanese Patent KOKAI Publication No. 5-192389.

Moreover, in Japanese Patent KOKOKU Publication No. 62-26787, there is proposed a catheter having double tube, which is inserted to the human body, and which is used to extract body fluids. In this case, its inner layer tube is formed of plastic material such as polyethylene or polyvinyl chloride.

If occlusion is caused by a change of a morbid state or a calculus in the biliary duct and the pancreatic duct, bile and pancreatic juice do not flow. As a result, a disease such as jaundice or pancreatitis occurs. At this time, there is known that the indwelling tube is placed in the biliary duct or the pancreatic duct to discharge body fluids.

However, in the conventional indwelling tube as shown in Japanese Utility Model KOKAI Publication No. 60-180442, and Japanese Patent KOKOKU Publication No. 62-26787, bacteria and matters in the bile and pancreatic juice are easily adhered onto the tube for an indwelling period of time. Then, due to the reduction of the diameter of the inner cavity of the tube and occlusion, the original object of discharging the bile and pancreatic juice cannot smoothly performed. As a result, there is a problem in which the disease recurs.

As bacteria and matters in the bile and pancreatic juice, there can be considered bacteria such as Escherichia coil (E. coli), enterrococcus, which enter at a tube insertion time for some reason, and lipid such as protein such as mucin in the bile and pancreatic juice, neutral fat, lecitin, cholesterol, etc.

On the other hand, in the indwelling tube shown in Japanese Patent KOKAI Publication No. 5-192389 and Japanese Utility Model KOKOKU Publication No. 6-1706, the inner layer of the tube is formed of fluoride resin having small surface energy (that is, wettability is low and matter is not easily adhered) to prevent the inner cavity of the tube from being clogged.

Thus, in the prior art, the material of the tube was reviewed in order to prevent the tube from being clogged. However, since the indwelling tube is placed in the body for a relatively long period of time, the generation of the clogging of the inner cavity of the tube cannot be completely restrained. AT the present time, no satisfiable indwelling tube is provided. Therefore, it has been desired that the indwelling tube, which is not easily clogged, be provided.

BRIEF SUMMARY OF THE INVENTION

An object of the present invention is to provide an indwelling tube having an inner surface characteristic in which roughness of a concave and convex portion of an inner cavity of the tube is controlled to prevent the inner cavity from being clogged with bacteria and matters, so that body liquid can easily flow.

According to the present invention, there is provided a medical indwelling tube for forming a passage at a predetermined portion where the tube is placed, comprising:

a tube member having at least an inner surface portion of an inner cavity formed of thermal plastic resin; and means for setting surface roughness of the inner surface of the tube member to 0.5 $\mu$m or less by an expression of maximum height Ry.

Moreover, according to the present invention, there is provided a medical indwelling tube for forming a passage at a predetermined portion where the tube is placed, comprising:

a tube member having at least an inner surface portion of an inner cavity formed of thermal plastic resin; and means for setting surface roughness of the inner surface of the tube member to 0.5 $\mu$m or less and more than 0.2 $\mu$m by an expression of maximum height Ry.

Moreover, according to the present invention, there is provided a medical indwelling tube for forming a passage at a predetermined portion where the tube is placed, comprising:

a tube member having at least an inner surface portion of an inner cavity formed of thermal plastic resin; and means for setting surface roughness of the inner surface of the tube member to 0.5 $\mu$m or less and more than 0.02 $\mu$m by an expression of maximum height Ry.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 11 is a microphotograph of 30000 magnifications of the surface of sample A after the experiment;

FIG. 12 is a microphotograph of 200 magnifications of a surface of sample B before an experiment;

FIG. 13 is a microphotograph of 5000 magnifications of the surface of sample B after the experiment;

FIG. 14 is a microphotograph of 30000 magnifications of the surface of sample B after the experiment;

FIG. 15 is a microphotograph of 200 magnifications of a surface of sample C before an experiment;

FIG. 16 is a microphotograph of 5000 magnifications of the surface of sample C after the experiment;

FIG. 17 is a microphotograph of 30000 magnifications of the surface of sample C after the experiment;

FIG. 18 is a microphotograph of 200 magnifications of a surface of sample D before an experiment;

FIG. 21 is a microphotograph of 200 magnifications of a surface of sample E before an experiment;

FIG. 22 is a microphotograph of 5000 magnifications of the surface of sample E after the experiment;

FIG. 23 is a microphotograph of 30000 magnifications of the surface of sample E after the experiment;

FIG. 24 is a microphotograph of 200 magnifications of a surface of sample F before an experiment;

FIG. 27 is a microphotograph of 200 magnifications of a surface of sample G before an experiment;

FIG. 28 is a microphotograph of 5000 magnifications of the surface of sample G after the experiment.

DETAILED DESCRIPTION OF THE INVENTION

Figure 1:
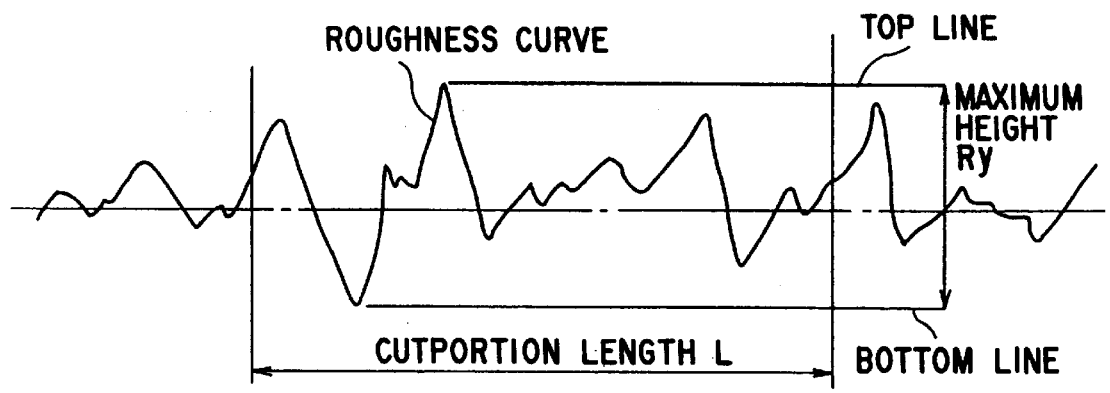
FIG. 1 is a view explaining maximum height Ry showing a surface roughness of an inner cavity of an indwelling tube of the present invention.

For example, a clogging phenomenon mechanism in an endoscopic retrograde biliary drainage tube, according to the general understanding, is considered as follows:

Specifically, bacteria and various matters such as protein and lipid are repeatedly adhered on an inner surface of the tube to generate a deposit layer. Then, an inner cavity of the indwelling tube is gradually clogged with the deposit layer.

Also, even in the indwelling tube, which is formed of fluoride resin having small surface energy, if the bacteria, passing through the inner cavity of the tube, and the matter such as protein and lipid are once adhered to the inner surface of the tube, the adhesion of these matters advances, and the bacteria and the protein and lipid are deposited on the inner surface of the tube. Finally, the inner cavity of the tube is clogged.

Such the clogging of the indwelling tube is specifically explained in "The Role of Bacteria for Occusion of Endoscopic Retrograde Biliary Drainage (ERBD) Tube" (Takeshi SHIGENO, Gastroenterogical Endoscopy, Vol. 1, 32 (2), pp. 345 to 352, 1990).

More specifically, according to the above document, at the time of first adhering the bacteria and the matters to the inner surface of the tube, the bacteria and the matters such as protein and lipid differ in their adhesion property, and the following unique process can be understood:

Specifically, among the bacteria and protein and the lipid, the bacteria are most easily adhered to the inner surface of the tube at a first process. Due to this, the bacteria are more widely adhered thereto than the protein and lipid. At the next process, the protein and lipid are adhered on the bacteria or between the bacteria. The bacteria and the matters are gradually deposited through such two processes. At the first stage, the bacteria such as colon bacillus are more widely adhered than the protein and lipid. The adhesion of the bacteria triggers the deposition of the bacteria and the matters at the second process.

An inventor of the present invention paid attention to the following point:

Specifically, if the adhesion of the bacteria, which are first adhered to the inner surface of the indwelling tube, can be prevented, the clogging of the tube caused by the adhesion can be largely prevented.

As the result of reviewing the property of the inner surface of the indwelling tube, there was considered surface energy (wettability, which is shown by a contact angle) of the inner surface, and concave and convex of roughness of the inner surface as reasons of adhesion of bacteria to the inner surface. Then, of two reasons, it was found that the concave and convex of roughness of the inner surface was largely related to the adhesion of the bacteria to the inner surface of the indwelling tube in the range of surface energy (water contact angle=90 to 120°) of such as polyethylene, fluorine resin as a general tube material.

Then, the surface roughness was expressed by a maximum height Ry defined by JIS-B0601-1994, and the relationship between a value of the maximum height of the surface roughness and the adhesion of bacteria was reviewed. The following shows the international standard corresponding to JIS-B0601-1994:

ISO 468-1982 (Surface roughness-Parameters, their values and general rules for specifying requirements)

ISO 3274-1975 (Instruments for the measurement of surface roughness by the profile method-Contact (stylus) instruments of consecutive profile transformation-Contact profile meters, system M)

ISO 4287/1-1984 (Surface roughness-Terminology Part 1: Surface and its parameters)

ISO 4287/2-1984 (Surface roughness-Terminology Part 2: Measurement of surface roughness parameters)

ISO 4288-1985 (Rules and procedures for the measurement of surface roughness using stylus instruments)

In this case, as shown in FIG. 1, only a length L, which is used as a reference, is cut in a direction of its average line from a roughness curve of the surface. Then, a distance between a top line of the concave and convex of the cut portion and a bottom line is measured in a direction of a longitudinal magnification of the roughness curve. That is, the maximum height Ry means the measured value, which is expressed by micrometer ($\mu$m). Also, the roughness curve means a curve, which is obtained by removing a surface waviness, which is longer than a predetermined wavelength, from a cross-section curve of an inner cavity surface of the tube, which is measured by a roughness measuring device, by use of a phase compensation typed high-frequency filter.

Conventionally, the indwelling tube such as the drainage tube generally used is formed by extrusion-molding thermal plastic resin such as polyethylene or polyvinyl chloride. As a result of actually measuring the concave and convex of the roughness of the inner surface of the tube, the maximum height Ry was in the range of 2 $\mu$m to 5 $\mu$m.

On the other hand, the main bacteria (Enterococcus, Klebsiella, *Escherichia coil* (*E. Coli*), which constantly exist in the intestines and which may be adhered to the inner surface of the drainage tube, were surveyed from the document (Saikengaku Nyumon, Jan. 20, 1974, by Daizo Ushiba). As a result, in the intestines, coccus, bacillus, or spirillum existed, and their outer shapes were not defined. However, in this case, the smallest bacteria was *E. Coli*, and the size ranges from about (0.5 to 0.6)×(1.0 to 3.0) $\mu$m. Seeing the size of *E. Coli* from the minimum width, the value was 0.5 to 0.6 $\mu$m.

Next, the phenomenon of adhesion to the inner surface of the indwelling tube was reviewed. The size of the concave and convex portion of the inner surface of the general indwelling tube was 2 $\mu$m to 5 $\mu$m in its maximum height Ry. Seeing the size of the *E. Coli*, which most exists in a body cavity, from the minimum width, the value was 0.5 to 0.6 $\mu$m. In consideration of the relationship between both cases in the size, it was understood that the size of *E. Coli* was smaller than that of the concave and convex portion of the roughness of the tube inner surface.

In view of the above-mentioned point, it can considered that the adhering phenomenon to the inner surface of the indwelling tube occurs through the following two processes.

First, the bacteria are most easily adhered to the inner surface of the tube than the protein and lipid, and the bacteria are more widely adhered thereto than the protein and lipid.

Figure 2A:
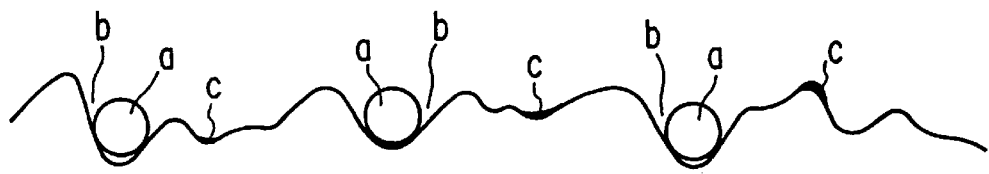
FIGS. 2A, 2B, and 2C are views explaining a phenomenon in which matters in body fluids are adhered to an inner surface of the medical indwelling tube.

Then, the size of bacteria a is slightly smaller than the size of a concave portion b of the convex and concave portion of the roughness of the inner surface of the tube. As a result, bacteria a just enter the concave portion b (FIG. 2A). In other words, bacteria a are just fitted to the concave portion b to be trapped. Since bacteria a can be seen as a lump of solid, bacteria cannot be easily escaped from the concave portion b. Then, most bacteria are trapped in the concave portion b of the inner surface of the indwelling tube and stay. Then, they are widely adhered to the inner surface of the tube.

Figure 2B:
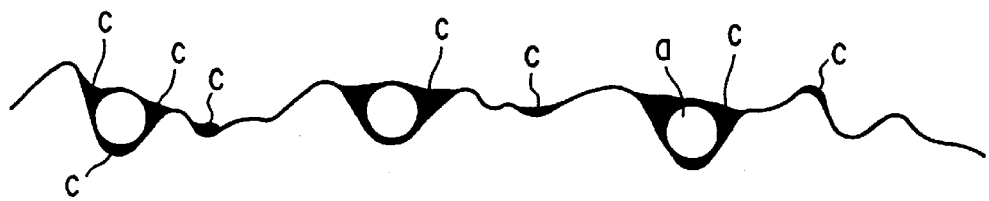

If bacteria a once start to be adhered to the inner surface of the indwelling tube, the protein and lipid c in bile and pancreatic juice start to be adhered around bacteria a since bacteria a are also formed of protein and lipid (FIG. 2B).

Figure 2C:
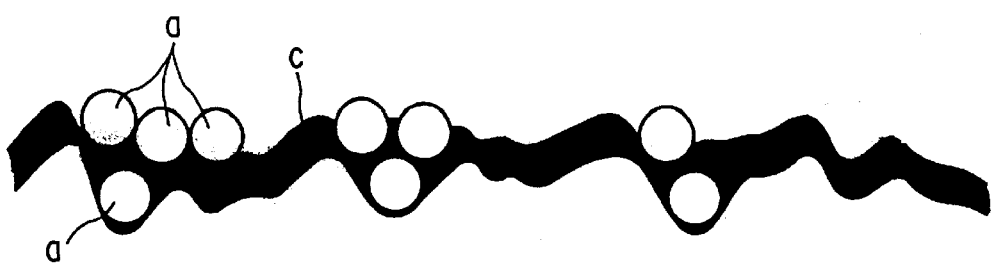

As a result, bacteria, and protein and lipid start to be sequentially adhered so as to completely fill the concave portion b. Then, the deposition of bacteria and lipid is started (FIG. 2C).

Thus, it can be considered that the bacteria, and the protein and lipid are deposited on the inner surface of the indwelling tube by a trapping phenomenon of bacteria. Then, it can be considered that the adhesive materials are layered and the inner cavity of the tube is clogged.

In conclusion, in the conventional indwelling tube, the maximum height Ry of the inner surface of the indwelling tube is larger than the size of the bacteria. Due to this, if the bacteria once enters the concave portion of the inner surface of the doweling tube, the bacteria are trapped by the concave portion, and they cannot be easily escaped from the concave portion. Then, the bacteria stay and are adhered to the inner surface of the tube, this quickens the deposition of the bacteria and the protein and lipid, and the inner cavity is finally clogged with the deposition.

The following shows an experiment for confirming whether the difference in the surface roughness of the inner surface of the tube influences the adhesion of the bacteria of the bile and pancreatic juice and matters such as the protein and lipid, and its result:

As a dummy sample for an experiment, six kinds of stainless steel sheets each having a different surface roughness (maximum height Ry) was used. To confirm whether or not the difference in the material, e.g., between metal and resin changes influence on the adhesion, one kind of tetrafluoroethylene/ perfluoroalkyl vinyl ether copolymer (PFA) sheet, which is fluorine resin, was used. In this case, if the tube-state sample is used, the tube must be cut to be expanded in examining the inner surface of the tube by an electonmicroscope later. In this case, there is a problem in which the state of the adhesion of the bacteria to the inner surface (peeling, omission, etc.,) is changed during the operation. For this reason, the sheet-like sample was used in this experiment. In this case, the stainless sheet was mainly used for the following reason.

Specifically, if the sheet-like sample, e.g., resin-made sample, is used, polishing cannot be accurately performed, and the necessary surface roughness cannot be obtained.

However, in this case, the experiment using stainless and resin (PFA) having the same level of the surface roughness was performed in advance. Then, it was confirmed that the adhesion state of the bacteria and the matters was unchanged in view of the difference in the material. The samples and the results are described later.

Table 1 shows the maximum height RY of each sample. The maximum height Ry was measured in accordance with the measuring method shown in JIS-0601-1994.

TABLE 1

|  | Sample Material | Maximum Height Ry ($\mu$m) |
| --- | --- | --- |
| Sample A | Stainless | 0.12 |
| Sample B | (SUS304-CSP-H) | 0.43 |
| Sample C |  | 1.12 |
| Sample D |  | 1.77 |
| Sample E |  | 2.55 |
| Sample F |  | 3.72 |
| Sample G | PFA | 0.94 |

The maximum height Ry was selected in the range, which is from the inner surface of the tube whose surface roughness is restrained the lowest value possible to the inner surface of the tube generally used.

Figure 8:
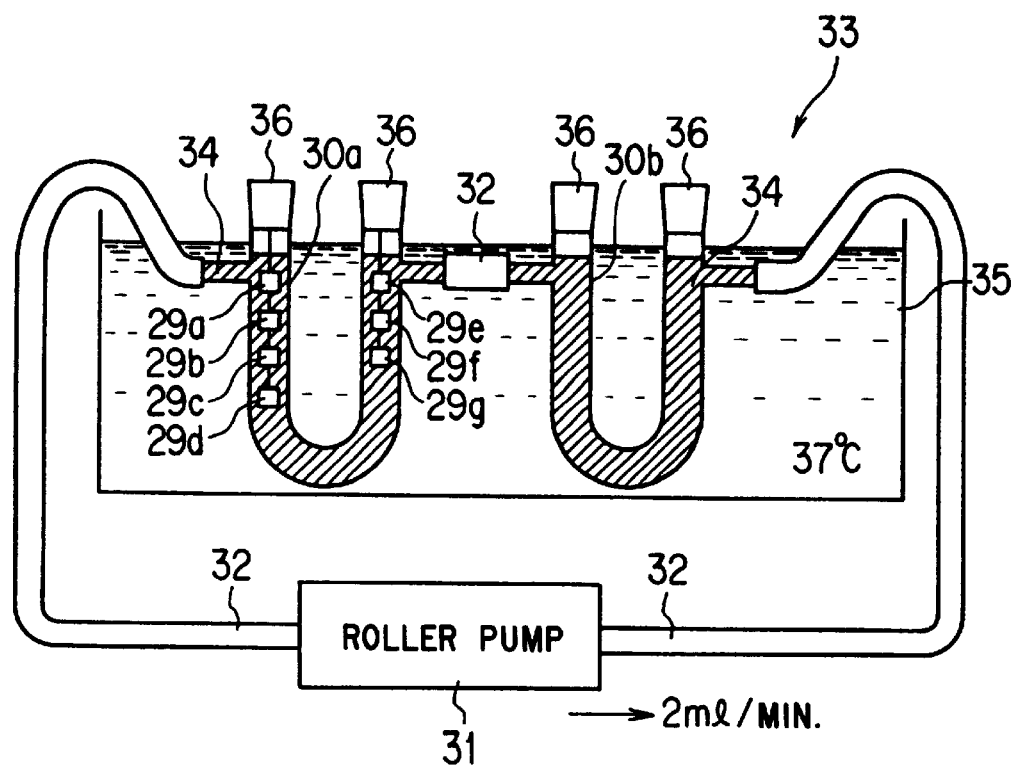
FIG. 8 is a view explaining an experimental system showing a relationship between a surface roughness and adhesion of bacteria and matters in bile.

FIG. 8 shows an experiment system. a glass U-shape tube 30a, having all samples 29a to 29g, a U-shape tube 30b, and a roller pump 31 are connected to each other by a plurality of silicon tubes 32 as shown in the figure to form a circulation device 33 in which fluid can be circulated. The roller pump 31 is actuated as using human bile 34 of human being is supplied to the U-shape tubes 30a and 30b such that the U-shape tubes 30a and 30b and the silicon tube 32 are filled with bile. In other words, the circulation line is filled with bile 34. The U-shape tube 30b is a reservoir vessel for circulating bile 34 as much as possible.

During the experiment, in order to set the temperature of bile 34 to the temperature under an actual internal environment, the U-shape pipes 30a and 30b are dipped in a water both 35, and water temperature of the water bath 35 is constantly maintained at 37° C.

The samples 29a to 29g are suspended with stainless wires in the U-shaped tube 30a not to contact each other. The U-shape tubes 30a and 30b are sealed with stoppers.

Moreover, during the experiment, the roller pump 31 is actuated at a fixed speed such that the circulation speed of bile 34 in the circulation device 33 is 2 m 1/min, which is substantially the same as a bile discharging speed in the body.

Under such a state, the samples 29a to 29g were left as they were for one week. Thereafter, the samples were collected, and the adhering state of the bacteria of bile and the matters to the surfaces of the samples was examined by the electromicroscope and photographed. The microphotographs can be shown in FIGS. 9 to 29.

Figure 9:
FIG. 9 is a microphotograph of 200 magnifications of a surface of sample A before an experiment.
Figure 10:
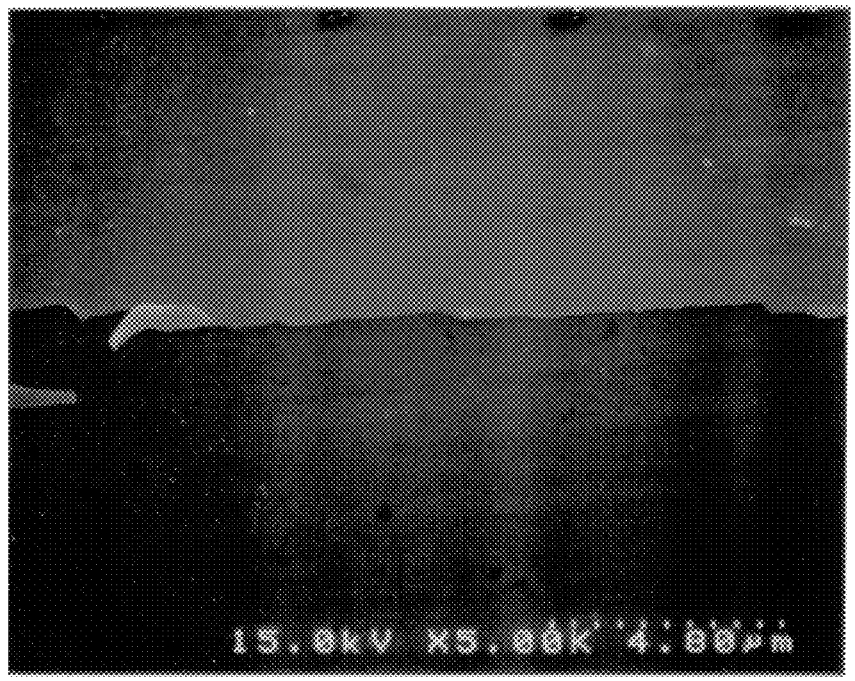
FIG. 10 is a microphotograph of 5000 magnifications of the surface of sample A after the experiment.
Figure 19:
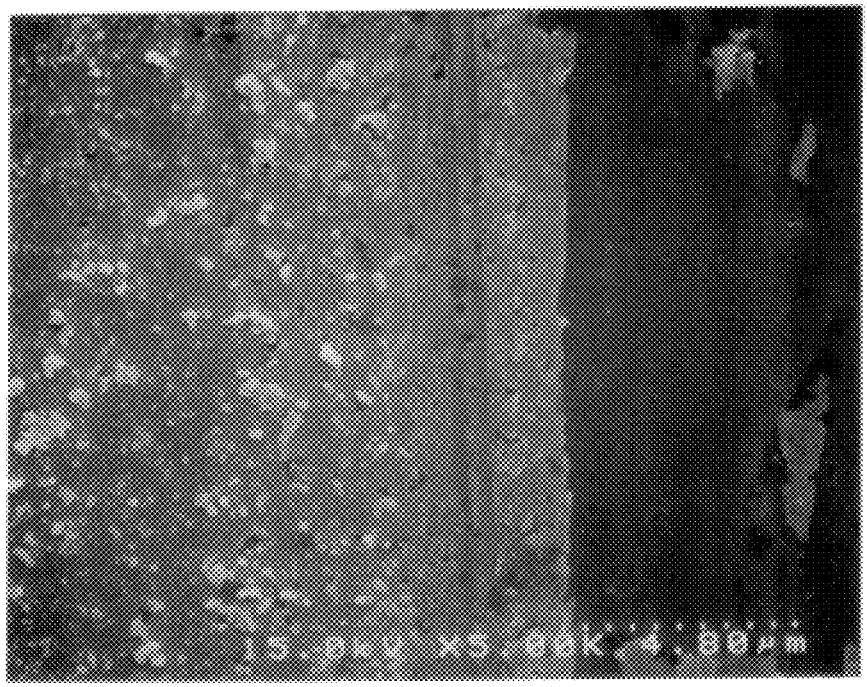
FIG. 19 is a microphotograph of 5000 magnifications of the surface of sample D after the experiment.
Figure 20:
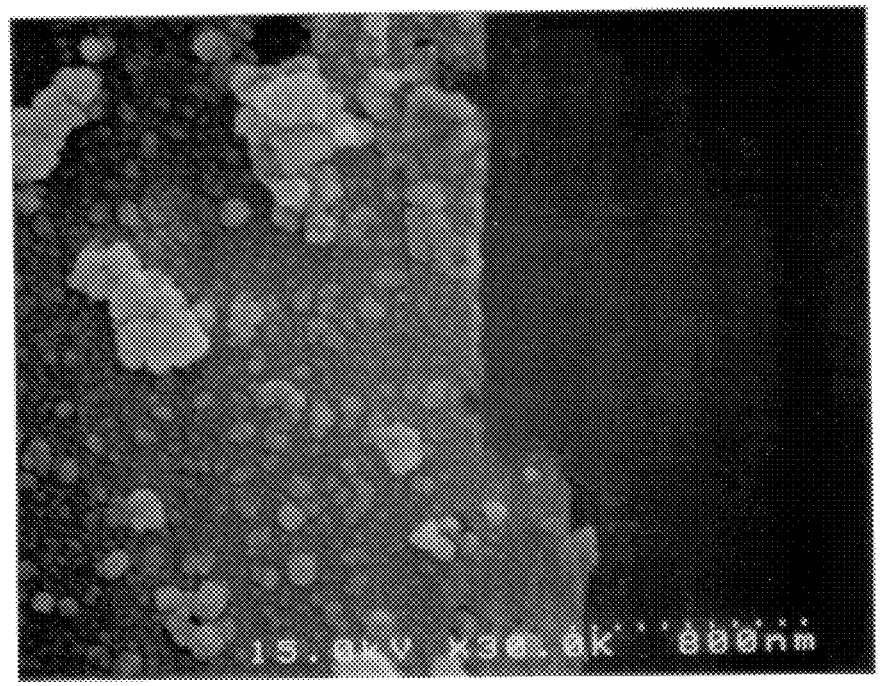
FIG. 20 is a microphotograph of 30000 magnifications of the surface of sample D after the experiment.
Figure 25:
FIG. 25 is a microphotograph of 5000 magnifications of the surface of sample F after the experiment.
Figure 26:
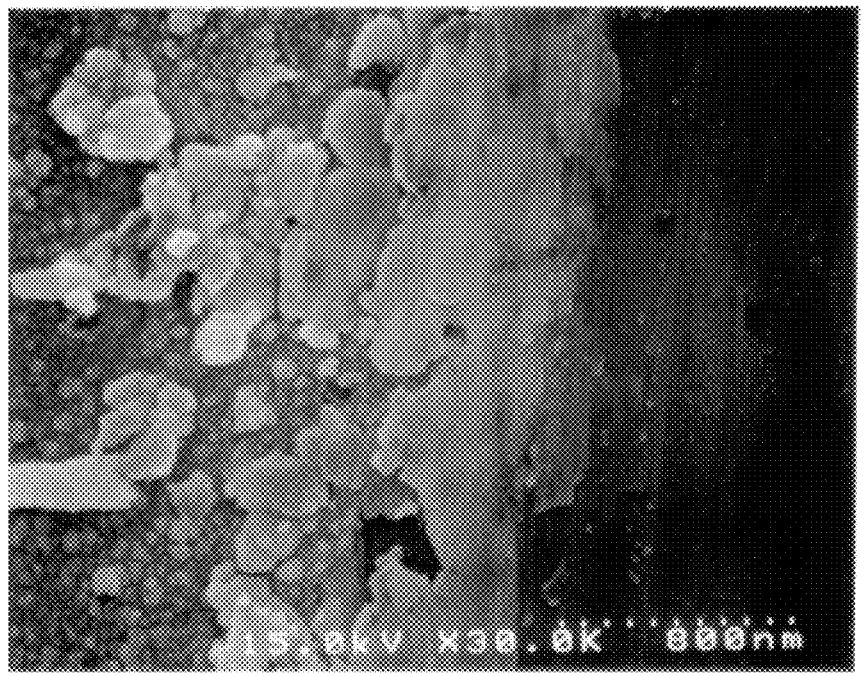
FIG. 26 is a microphotograph of 30000 magnifications of the surface of sample F after the experiment.
Figure 29:
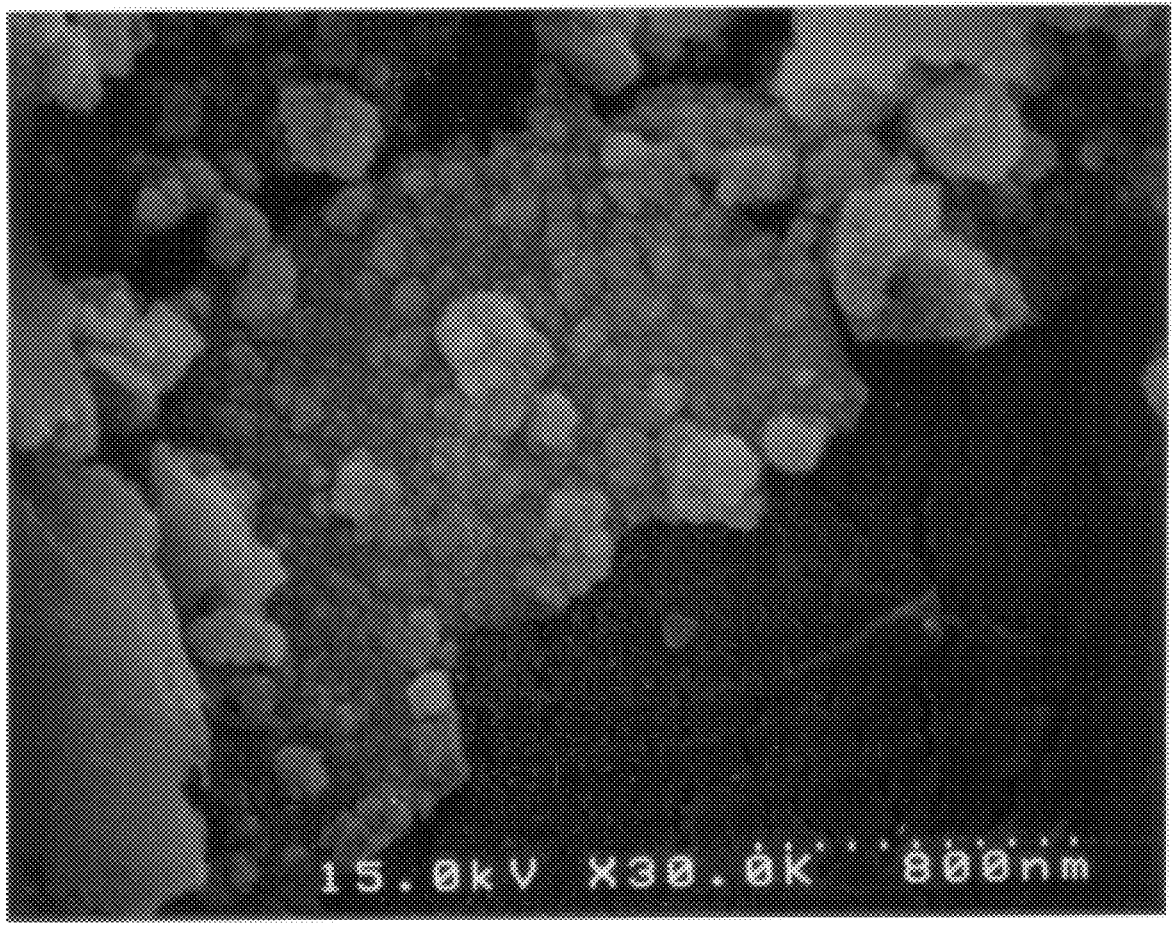
FIG. 29 is a microphotograph of 30000 magnifications of the surface of sample G after the experiment.

FIGS. 9 to 11 are microphotographs of sample A, FIGS. 12 to 14 are microphotographs of-sample B, FIGS. 15 to 17 are microphotographs of sample C, FIGS. 18 to 20 are microphotographs of sample D, FIGS. 21 to 23 are microphotographs of sample D,. FIGS. 24 to 26 are microphotographs of sample F, and FIGS. 27 to 29 are microphotographs of sample G.

FIGS. 9, 12, 15, 18, 21, 24, and 27 are photographs of 200 magnifications of a surface of each of samples A to G before an experiment.

To easily conform the adhesion state of the bacteria and the protein and lipid to the sample surface after the experiment, two kinds of photographs, that is, photograph of 5000 magnifications of each of samples A to G (FIGS. 10, 13, 16, 19, 22, 25, and 28) and that of 30000 magnifications (FIGS. 11, 14, 17, 20, 23, 26, and 29) were prepared. Each photograph was taken from the portion just above the surface of each sample. Moreover, regarding the photograph taken after the experiment, in order to clarify the adhesion state, the adhesion matter on the surface of the sample was partially cut, and the boundary between the portion where the adhesion matter was attached and the portion where no adhesion matter was attached was expanded and photographed.

Seeing the photographs of 5000 magnifications (FIGS. 10, 13, 16, 19, 22, 25, and 28) after the experiment and those of 30000 magnifications (FIGS. 11, 14, 17, 20, 23, 26, and 29) after the experiment, it can be understood that the adhesion matter is thin attached to the surface of each of the samples. Seeing from the photographs (FIGS. 10 and 11, and FIGS. 13 and 14) of samples A and B after the experiment, it can be understood that minute granules of the bacteria are scattered and adhered and the matters, which seem to be the protein and lipid, are adhered therebetween. As comparing the photographs (FIGS. 10 and 11, and FIGS. 13 and 14) of samples A and B after the ekperiment with the photographs (FIGS. 16 and 17, and FIGS. 19 and 20, FIGS. 22 and 23, FIGS. 25 and 26, and FIGS. 28 and 29) of samples C to G after the experiment, the following point can be understood:

Specifically, in the photographs of samples C to G, the large granules of the bacteria and the matters, which seem to be the protein and lipid, are adhered on the thin-layered adhesion, which can be seen in the photographs of samples A and B. Seeing the photograph (FIG. 14) expanded at 30000 magnifications, the granular matter is adhered on the thin-layered adhesion even in sample B. However, as compared with the size of the granular matter of the respective samples C to G (about 1 to 5 $\mu$m, (100 to 500 $\mu$m)), each the size of the granular matter of sample B is extremely small (about 0.1 to 0.2 $\mu$m (10 to 20 $\mu$m)).

Table 2 shows the surface roughness of each sample and the adhering state of the bacteria and the matters in bile.

TABLE 2

| Sample | Sample Material | Maximum Height Ry Height Ry ($\mu$m) | Adhesion State of Bacteria and Matter |
|---|---|---|---|
| Sample A | Stainless (SUS304-CSP-H) | 0.12 | minute granules of bacteria and matter, which seems to be in bile, is thin adhered |
| Sample B | | 0.43 | minute bacteria and granules of matter in bile are adhered on thin adhesion of sample A |
| Sample C | | 1.12 | large bacteria and granules of matter in bile are adhered on thin adhesion of sample A |
| Sample D | | 1.77 | ↓ |
| Sample E | | 2.55 | ↓ |
| Sample F | | 3.72 | ↓ |
| Sample G | PFA | 0.94 | ↓ |

From the result shown in Table 2, it can be understood that the adhesion of the bacteria and the matters in bile is not easily generated in the case in which the maximum height Ry is 0.5 $\mu$m or less as compared with the case in which the maximum height Ry is around 1 $\mu$m. As is obvious from the comparison between samples A and B, the adhesion of the bacteria and the matter is small in the case of sample A whose maximum height Ry is smaller. Moreover, the lower the surface roughness is, the slower the progress of the adhesion of the bacteria and the matters in bile becomes.

The above point can be used as data supporting the idea how to prolong the period of time until the inner cavity of the indwelling tube is clogged.

Thus, it was understood that the concave and convex portion (maximum height Ry) of the surface roughness of the indwelling tube conventionally used was larger than the size of the main bacteria constantly existing in the intestines, and the tube was easily clogged.

Then, the inventor of the present invention paid attention to the point that the size of the main bacteria existing in the intestines was about (0.5 to 0.6)×(1.0 to 3.0) $\mu$m. It was understood that the size of the concave and convex portion of the surface roughness of the indwelling tube (value of maximum height Ry) was desirably set to 0.5 $\mu$m or less to prevent the bacteria and the protein from being deposited by the trap phenomenon of the bacteria and to obtain a clogging prevention effect.

In the indwelling tube described in Japanese Utility Model KOKOKU Publication No. 6-1706 and Japanese Patent KOKAI Publication No. 5-192389, even in the case of using fluorine resin having small surface energy in place of the plastic material such as polyethylene, the clogging of the inner cavity was not sufficiently solved. The inventor of the present invention understood that the reason of the clogging of the inner cavity lay in the property of the concave and convex portion of the surface of the indwelling tube (roughness of the inner surface) from the above-explained result.

According to the present invention, there can be provided a medical indwelling tube having an inner surface characteristic in which roughness of the concave and convex portion of the inner surface of the tube is controlled to prevent bacteria and matters such as protein and lipid passing through body liquids from being easily adhered to the inner surface so that the inner cavity is not easily clogged. Then, the inner surface roughness of the inner cavity of the indwelling tube is set to a value which shows that bacteria in the body liquids are not adhered. Thereby, it is possible to prevent the deposition of matters on the inner surface of the tube, which is caused by a phenomenon in which bacteria in the body liquids are adhered. More specifically, the roughness of the inner surface of the indwelling tube, that is, a value of maximum height Ry is set to 0.5 μm or less, thereby realizing the indwelling tube having the clogging prevention effect in which the inner cavity of the tube can be greatly prevented from being clogged.

EMBODIMENT 1

Figure 3:
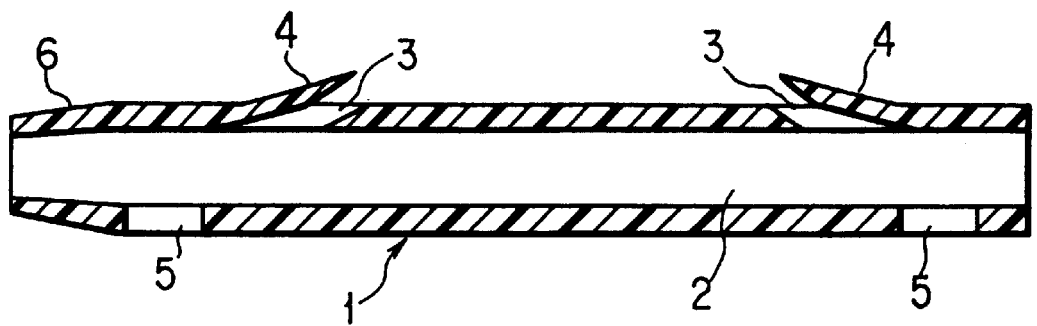
FIG. 3 is a vertical cross-sectional view of the indwelling tube of a first embodiment of the present invention.

A first embodiment will be explained with reference to FIGS. 3 and 4.

The first embodiment relates to an indwelling tube 1 for a biliary drainage (ERBD tube) 1. The tube 1 is a single layer tube, which is formed of plastic resin material such polyethylene, and which has an inner diameter of 2.4 mm and an outer diameter of 3.2 mm. Then, at least inner surface portion of the inner cavity of the tube is formed of thermal plastic resin. Regarding the roughness of the inner surface of an inner cavity 2 of the tube 1, the value of the maximum height Ry is 0.5 μm or less. The value of the maximum height Ry is desirably set as small as possible in the range that the tube can be formed.

For forming the single-layered indwelling tube 1, a core wire, which is finished to be a mirror surface, is coated with resin material. Then, resin material is hardened so that the tube-like material is formed. Thereafter, both sides of the core wire is drawn. The outer diameter of the core wire is thinned to be pulled out. As a result, only a tube is left, and the concave and convex portion of the surface roughness of the core wire is transferred onto the inner surface of the inner cavity of the tube, so that the indwelling tube having a predetermined roughness can be obtained.

Regarding the surface roughness of the inner surface of the tube, the value of about 0.02 μm can be obtained in the range of the mechanical processing limit of the mirror-surface finishing of the core wire. In this case, if the value is 0.2 μm or more, the mirror-surface finishing of the outer peripheral surface of the core wire can be easily processed and maintained, and this value is desirable in processing the indwelling tube.

On the peripheral wall portions close to both front and back end portions of the tube 1, cut portions 3 are formed. Thereby, side flaps 4 are formed to be freely opened and closed. The cut portions 3 are directed to the front and back ends and inclined in a deeper cutting direction to be wedge-shaped. Moreover, separately from the side flaps 4, side holes 5 are formed on the peripheral wall portions close to both front and back end portions of the tube 1. The front end portion of the tube 1 is tapered and used as a taper portion 6.

Figure 4:
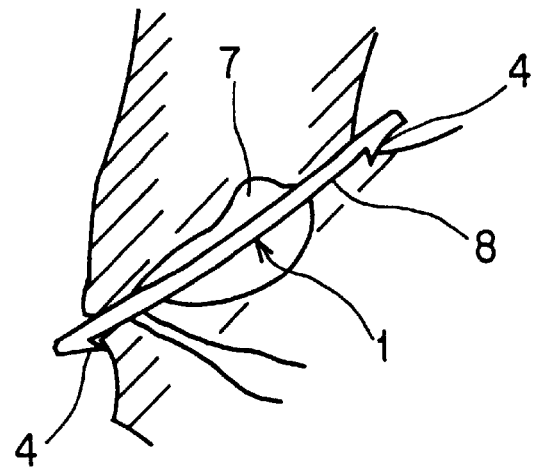
FIG. 4 is a view explaining a using state of the indwelling tube for a biliary drainage of the first embodiment of the present invention.

The above-structured indwelling tube 1 is endoscopically inserted to a strangulated portion 8 of a biliary duct 7 from the duodenum of the body through the insertion channel of the endoscope as shown in FIG. 4 so as to be placed at a predetermined position. Then, discharge of e.g., bile can be performed for a long period time through the inner cavity of the tube 1. Therefore, the generation of jaundice can be prevented.

In this case, since the value of the maximum height Ry of the surface roughness of the inner surface of the tube 1 is set to 0.5 μm or less, the adhesion of the bacteria in the bile, which is the cause of clogging the tube 1, is not easily generated. As a result, the period of time until the inner cavity 2 is clogged is prolonged.

The tube 1 is surely fixed to the biliary duct 7 by the side flaps 4, so that the generation of the positional shift can be prevented. Moreover, since side holes 5 are formed on the peripheral wall portions close to both front and back end portions of the tube 1, separately from the side flaps 4, the discharge of bile can be efficiently performed. Also, since the front end portion of the tube 1 is tapered and used as the taper portion 6, the tube 1 can be easily inserted through the strangulated portion 8 of the biliary duct 7.

EMBODIMENT 2

Figure 5:
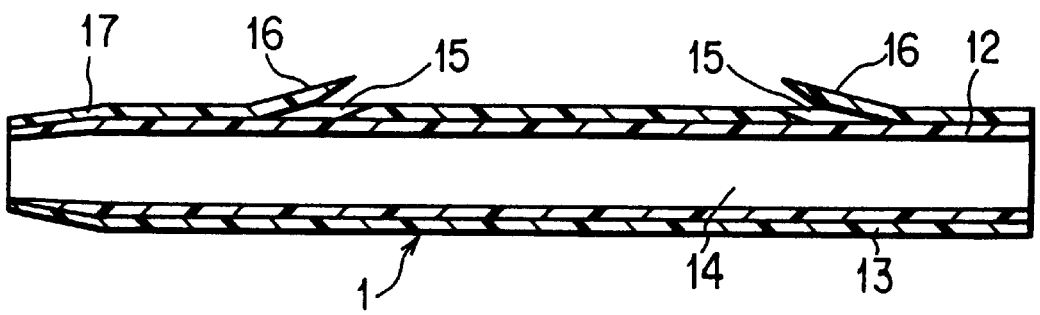
FIG. 5 is a vertical cross-sectional view of the indwelling tube of a second embodiment of the present invention.

A second embodiment will be explained with reference to FIG. 5.

The second embodiment relates to an indwelling tube 11 for a biliary drainage. The tube 11 has a two-layer structure having an inner layer tube 12 and an outer layer tube 13. The inner layer tube 12 is formed of plastic resin material, that is polytetrafluoroethylene (PTFE), and the outer layer tube 13 is formed of plastic resin material, that is, polyethylene. Regarding the roughness of the inner surface of an inner cavity 14 of the inner layer tube 12, the value of the maximum height Ry is 0.5 μm or less. The inner layer tube 12 can be formed by the tube manufacturing method of the first embodiment.

On the peripheral wall portions close to both front and back end portions of the tube 13, cut portions 15 are formed. Thereby, side flaps 16 are formed to be freely opened and closed. The cut portions 15 are directed to the front and back ends and inclined in a deeper cutting direction to be wedge-shaped. The cutting portions 15 do not extend to the inner-layer tube 12. The front end portion of the tube 11 is tapered and used as a taper portion 17. Then, similar to the first embodiment, the above-structured indwelling tube 11 is positioned at the strangulated portion of the biliary duct so as to discharge bile. In this case, since the value of the maximum height Ry of the surface roughness of the inner surface of the tube 11 is set to 0.5 μm or less, the adhesion of the bacteria in the bile, which is the cause of clogging the tube 11, is not easily generated. As a result, the period of time until the cavity of the tube is clogged is prolonged.

Since the side flaps 16 are formed on the peripheral wall portions close to both front and back end portions of the tube 13, the tube 11 is surely fixed to the biliary duct without generating the positional shift. Moreover, as compared with PTFE single indwelling tube containing contrast medium, the indwelling tube 11 is flexible, the tube 11 can be extremely easily positioned at the body cavity. Also, by changing a thickness ratio between the inner-layer tube 11 and the outer-layer tube 13, flexibility of the tube 11 can suitably adjusted. Since the side flaps 16 and the side holes are not formed in the inner layer tube 12, no burr is not generated on the inner cavity at the time of processing.

Therefore, the adhesion of the bacteria, and protein and lipid is not easily generated. As a result, the period of time until the inner cavity 14 of the tube 11 is clogged due to the repetition of the adhesion is prolonged. Moreover, since the front end portion of the tube 11 is tapered and used as the taper portion 17, the tube 11 can be easily inserted through the strangulated portion of the biliary duct.

EMBODIMENT 3

Figures 6, 7:
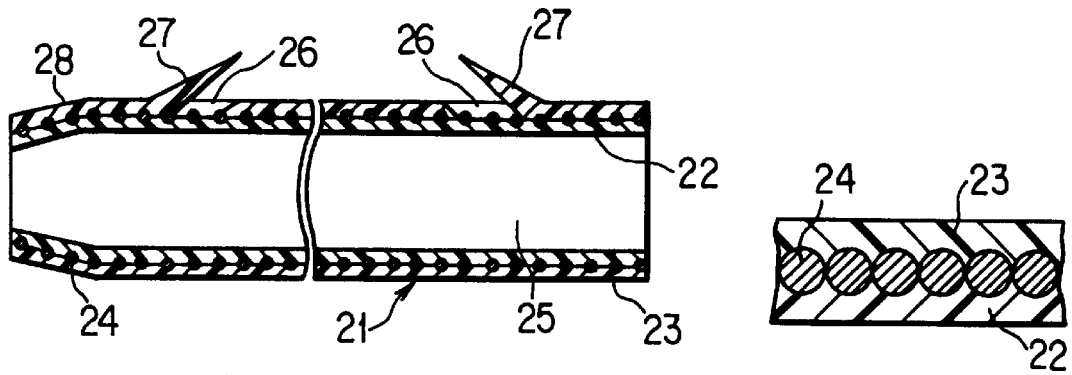
FIG. 6 is a vertical cross-sectional view of the indwelling tube of a third embodiment of the present invention.
FIG. 7 is a cross-sectional view partially enlarging the indwelling tube of the third embodiment of the present invention.

A third embodiment will be explained with reference to FIGS. 6 and 7.

The third embodiment also relates to an indwelling tube 21 for a biliary drainage. The indwelling tube 21 has an inner-layer tube 22 and an outer-layer tube 23. Moreover, a reinforcing member 24 is provided between the inner-layer tube 22 and the outer-layer tube 23. The inner-layer tube 22 is formed of plastic material, that is polytetrafluoroethylene (PTFE), and the outer layer tube 23 is formed of plastic material, that is, polyethylene. The reinforcing member 24 is formed of cylindrical blade, which is woven of a thin metal line in a lattice shape.

The inner-layer tube 22 can be formed by the tube manufacturing method of the first embodiment. Then, the surface roughness of the inner surface of the inner cavity 25 of the inner-layer tube 22, that is, the value of the maximum height Ry is 0.5 µm or less.

On the peripheral wall portions close to both front and back end portions of the tube 23, cut portions 26 are formed. Thereby, side flaps 27 are formed to be freely opened and closed. The cut portions 26 are directed to the front and back ends and inclined in a deeper cutting direction to be wedge-shaped. The cutting portions 26 do not extend to the reinforcing member 24 and the inner-layer tube 22. The front end portion of the tube 21 is tapered and used as a taper portion 28.

The above-structured indwelling tube 21 is positioned at the strangulated portion of the biliary duct so as to discharge bile. In this case, since the value of the maximum height Ry of the surface roughness of the inner surface of the tube 21 is set to 0.5 µm or less, the adhesion of the bacteria in the bile, which is the cause of clogging the tube 21, is not easily generated. As a result, the period of time until the cavity of the tube is clogged is prolonged.

Since the side flaps 27 are formed on the peripheral wall portions close to both front and back end portions of the tube 23, the tube 21 is surely fixed to the biliary duct without generating the positional shift. Moreover, as compared with PTFE single indwelling tube containing contrast medium, the indwelling tube 21 is flexible, the tube 21 can be extremely easily positioned at the body cavity. Also, by suitably changing a thickness ratio between the inner-layer tube 22 and the outer-layer tube 23, and the diameter of the metal wire of the reinforcing member 24, flexibility of the tube 21 can suitably adjusted.

Since the side flaps 27 and the side holes are not formed in the inner layer tube 21, no burr is not generated on an inner cavity 25 at the time of processing.

Therefore, the adhesion of the bacteria, and protein and lipid is not easily generated. As a result, the period of time until the inner cavity 25 of the tube 21 is clogged due to the repetition of the adhesion is prolonged.

As motioned above, the cut portions 26 are formed on the outer-layer tube 23 by a cutter so as to form the side flaps 27. In this case, since the reinforcing member 24 serves as a stopper, and the inner-layer tube 22 is not damaged, the side flap forming can be very easily performed. Moreover, the reinforcing member 24 can greatly increase flexibility of the tube 21. Due to this, if the inner-layer tube 22 is extremely thinned to increase the thickness of the outer-layer tube 23, the side flaps 27 can be reinforced. As a result, the engaging force of the tube 21 to the body cavity is increased, the tube 21 can be surely fixed thereto. Moreover, since the inner-layer tube 22 and the outer-layer tube 23 are inserted to be bonded to the concave portion of the outer periphery formed by the reinforcing member 24, the bonding force can be greatly increased. Moreover, since the front end portion of the tube 21 is tapered and used as the taper portion 28, the tube 21 can be easily inserted through the strangulated portion of the biliary duct.

MODIFICATIONS OF THE EMBODIMENTS

The reinforcing member 24 of the third embodiment may be formed of a coil, or a flex member, etc.

The indwelling tube of the first embodiment, the inner-layer tube and the outer-layer tube of the second embodiment are not limited to the materials described in these embodiments. These tubes may be formed of tetrafluoroethylene/perfluoroalkyl vinyl ether copolymer (PFA), tetrafluoroethylene/hexafluoropropylene copolymer (FEP), polyvinyl chloride, polystyrene, polystyrene series elastmer, polyamide, polyamide series elastmer, olefin series (e.g., EVA, polypropylene) other than polyethylene, olefin series elastmer other than polyethylene, polyethylene terephthalate, polyethylene terephthalate series elastmer, and other thermal plastic resin.

The size of each of the outer and inner diameters of the indwelling tube of the first embodiment is not limited to the values described in the first embodiment. These sizes can be freely selected in the range of about 1 to 30 mm.

In the present invention, the value, 0.5 µm or less of the surface roughness of the inner surface of the inner cavity of the indwelling tube is desirably set to the entire surface of the inner surface of the indwelling tube. However, the value is not limited to the entire surface.

As explained above, according to the indwelling tube of the present invention, the bacteria and the matters, e.g., protein and lipid are not easily adhered to the inner cavity of the tube, thereby making it possible to prolong the period of time until the inner cavity of the indwelling tube is clogged.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. A medical indwelling tube for forming a passage through which fluids pass at a predetermined portion where said tube is placed, comprising:

a tube member having at least an inner surface portion of an inner cavity formed of thermal plastic resin; and means for setting surface roughness of the inner surface of said tube member to 0.5 µm or less by an expression of maximum height Ry, thereby preventing deposition of bacteria and matters in fluids on the inner surface of said tube caused by a bacteria adhering phenomenon.

2. A medical indwelling tube for forming a passage through which fluids at a predetermined portion where said tube is placed, comprising:

a tube member having at least an inner surface portion of an inner cavity formed of thermal plastic resin; and means for setting surface roughness of the inner surface of said tube member to 0.5 µm or less by an expression of maximum height Ry, thereby preventing deposition of bacteria and matters in fluids on the inner surface of said tube caused by a bacteria adhering phenomenon where said maximum height Ry is a value, which can be obtained by cutting only a reference length in a direction of its average line from a roughness curve of the surface, and by measuring a distance between a top line of the cut portion and a bottom line in a direction of a longitudinal magnification of a roughness curve.

3. The tube according to claim 1, wherein the surface roughness of the inner surface of said tube member is set to 0.5 μm or less and more than 0.2 μm by an expression of maximum height Ry.

4. The tube according to claim 1, wherein the surface roughness of the inner surface of said tube member is set to 0.5 μm or less and more than 0.02 μm by an expression of maximum height Ry.

5. The tube according to claim 1, wherein said tube member is formed of a single layer tube made of thermal plastic resin.

6. The tube according to claim 1, wherein said tube member has a double tube structure having an outer-layer tube and an inner-layer tube, and only the inner-layer tube is formed of thermal plastic resin.

7. The tube according to claim 1, wherein said tube member has a double tube structure having an outer-layer tube and an inner-layer tube, and a reinforcing member is provided between said outer-layer tube and the inner-layer tube.

* * * * *